United States Patent
Ferreira et al.

(10) Patent No.: US 11,589,779 B2
(45) Date of Patent: Feb. 28, 2023

(54) FINGER SEGMENT TRACKER AND DIGITIZER

(71) Applicants: Louis Ferreira, London (CA); Ryan Kope, London (CA)

(72) Inventors: Louis Ferreira, London (CA); Ryan Kope, London (CA)

( * ) Notice: Subject to any disclaimer, the term of this patent is extended or adjusted under 35 U.S.C. 154(b) by 950 days.

(21) Appl. No.: 16/422,286

(22) Filed: May 24, 2019

(65) Prior Publication Data

US 2019/0274590 A1    Sep. 12, 2019

Related U.S. Application Data

(62) Division of application No. 15/036,244, filed as application No. PCT/CA2014/051050 on Oct. 31, 2014, now Pat. No. 10,342,458.
(Continued)

(51) Int. Cl.
*A61B 5/107*    (2006.01)
*A61B 5/00*    (2006.01)
(Continued)

(52) U.S. Cl.
CPC .......... *A61B 5/1077* (2013.01); *A61B 5/0053* (2013.01); *A61B 5/107* (2013.01);
(Continued)

(58) Field of Classification Search
CPC ..... A61B 5/1077; A61B 5/0053; A61B 5/107; A61B 5/6826; A61B 2034/2068;
(Continued)

(56) References Cited

U.S. PATENT DOCUMENTS

| 5,895,871 A | 4/1999 | Patton et al. |
| 6,236,037 B1 | 5/2001 | Asada et al. |

(Continued)

FOREIGN PATENT DOCUMENTS

| JP | 11024873 | 1/1999 |
| JP | 2001104256 A | 4/2001 |

(Continued)

OTHER PUBLICATIONS

ISA/CA. "International Search Report and Written Opinion", for International Application No. PCT/CA2014/051050, 8 Pages.

*Primary Examiner* — Daniel L Cerioni
(74) *Attorney, Agent, or Firm* — Brion Raffoul

(57) ABSTRACT

Systems, methods, and devices relating to a sensor array for use with a user's finger segment and which indirectly maps the topography of a surface under the finger segment. Each sensor array is worn on a user's finger segment and has multiple sensitive strain gauges as well a positioning sensor. The multiple strain gauges are deployed around the periphery or sides of the finger segment. Each strain gauge measures the deformation of the finger segment pad as the finger segment passes over the surface topography. The relative ratios of the deformation detected indicates the location of a feature or contact point on the topography relative to the group of strain gauges. The positioning sensor determines the array's orientation as well as its location relative to a predetermined global reference frame.

3 Claims, 5 Drawing Sheets

Related U.S. Application Data

(60) Provisional application No. 61/903,622, filed on Nov. 13, 2013.

(51) Int. Cl.
  *G01L 5/00* (2006.01)
  *G06F 3/01* (2006.01)
  *G06F 3/0346* (2013.01)
  *A61B 34/20* (2016.01)

(52) U.S. Cl.
  CPC .............. *A61B 5/6826* (2013.01); *G01L 5/00* (2013.01); *G06F 3/014* (2013.01); *G06F 3/017* (2013.01); *G06F 3/0346* (2013.01); *A61B 2034/2068* (2016.02); *A61B 2562/0261* (2013.01); *A61B 2562/066* (2013.01)

(58) Field of Classification Search
  CPC ...... A61B 2562/0261; A61B 2562/066; G01L 5/00; G06F 3/107
  See application file for complete search history.

(56) References Cited

U.S. PATENT DOCUMENTS

| | | | |
|---|---|---|---|
| 6,388,247 B2 | 5/2002 | Asada et al. | |
| 7,742,802 B2 | 6/2010 | Green, II et al. | |
| 2005/0052412 A1 | 3/2005 | McRae et al. | |
| 2005/0199250 A1* | 9/2005 | Green | A61B 34/20 128/899 |
| 2006/0119578 A1 | 6/2006 | Kesavadas et al. | |
| 2006/0129070 A1* | 6/2006 | Pearl | A61B 5/418 600/595 |
| 2009/0278798 A1 | 11/2009 | Kim et al. | |
| 2011/0006902 A1* | 1/2011 | Saigh | A61B 5/6826 340/573.1 |
| 2012/0259239 A1 | 10/2012 | Chenaux et al. | |

FOREIGN PATENT DOCUMENTS

| | | |
|---|---|---|
| JP | 2001265522 A | 9/2001 |
| WO | 2012173254 A1 | 12/2012 |

* cited by examiner

FINGER SEGMENT TRACKER AND DIGITIZER

RELATED APPLICATIONS

This application is a Divisional of U.S. patent application Ser. No. 15/036,244 filed on May 12, 2016 which is a US National Stage (371) of PCT/CA2014/051050 filed on Oct. 31, 2014 which claims priority from U.S. Provisional Patent Application No. 61/903,622 filed on Nov. 13, 2013.

TECHNICAL FIELD

The present invention relates to sensor arrays. More specifically, the present invention relates to devices and systems which can be used with a user's finger or finger segments for mapping the shape and topography of a surface.

BACKGROUND OF THE INVENTION

During surgery or preparatory to surgery, a surgeon may need to determine the surface topography of the tissue to be operated on. As an example, orthopedic surgeons may need to determine the surface of bones which may need to be operated on. In some cases, a surgeon may need to digitize the surface of a patient's bone in order to make measurements, or to apply a pre-operative plan for computer-assisted surgery. A pre-operative plan might be the desired location of a bone cut or the final location of an implant, or any number of desired outcomes.

A pre-operative plan is usually determined using a CT (computed-tomography) scan or MRI (magnetic resonance image) of the patient's anatomy. The pre-operative plan can include desired changes to the anatomy, or navigational marks, or it can include a virtual representation of an implant in the desired final location. In computer-assisted surgery, an important step is to transfer the pre-operative plan to the patient's anatomy during the surgery, so that the surgeon can view it on a monitor and so that the navigational software can correlate the plan to the patient. Currently, such computer- or robot-assisted surgical protocols for orthopaedic surgery utilize a long physical contact stylus to digitize the bone surface. This process requires an unobstructed view of the entire bony surface, which necessitates a large surgical opening. For many reasons, large surgical openings are not desired and current surgical trends are toward minimally invasive surgery.

Based on the above, there is therefore a need for systems, methods, or devices which allows surgeons to map the topography of areas which may be operated on. Specifically, there is a need for such technologies which do not involve large surgical openings.

SUMMARY OF INVENTION

The present invention provides systems, methods, and devices relating to a sensor array for use with a user's finger segment and which maps the topography of a surface under the finger segment while simultaneously measuring the finger contact force and the location of the net point of contact. Each sensor array is worn on a user's finger segment and has multiple sensitive strain gauges as well a positioning sensor. The multiple strain gauges are deployed around the periphery or sides of the finger segment. Each strain gauge measures the deformation of the finger segment pad as the finger segment passes over the surface topography. The relative ratios of the deformation detected indicates the net location of contact on the surface relative to the group of strain gauges. The positioning sensor determines the array's orientation as well as its location relative to a predetermined global frame of reference, which may be established anywhere, including other objects or anatomical structures such as bones or body segments. Upon calibration, the net point of contact measured relative to the group of gauges is transformed by the system and is determined relative to the global reference frame.

Using specific methods, the system (hardware and software) is calibrated to report contact force and the location of the net point of contact in real physical units. The contact force, for each finger segment wearing a calibrated device, is reported as a function of overall finger tissue deformation as detected by the strain gauges.

In a first aspect, the present invention provides a device for determining features on a surface using a user's finger segment, the device comprising:
  a plurality of sensors for detecting a deformation of a pad on said finger segment, at least two of said plurality of sensors being located at sides of said finger segment;
  a positional sensor for determining a location of said device relative to a predetermined reference frame;
  wherein
  for each of said plurality of sensors, a sensor produces a signal proportional to an amount of said deformation detected and proportional to a distance between said deformation and said sensor.

In a second aspect, the present invention provides a system for measuring force exerted on multiple fingers of a user, the system comprising:
  a plurality of devices for detecting and measuring force on one of said user's finger segments, each device comprising:
    a plurality of sensors for detecting a deformation of a pad on a finger segment, at least two of said plurality of sensors being located at sides of said finger segment, each one of said plurality of sensors producing a signal proportional to an amount of said deformation detected and proportional to a distance between said deformation and said one of said plurality of sensors;
    a positional sensor for determining a location and orientation of said device, and said point of contact on the surface, relative to a predetermined reference frame;
  wherein
  each of said plurality of devices is deployed on a separate finger segment of said user.

BRIEF DESCRIPTION OF THE DRAWINGS

The embodiments of the present invention will now be described by reference to the following figures, in which identical reference numerals in different figures indicate identical elements and in which.

DETAILED DESCRIPTION

The present invention is a unique technology that provides both accurate 3D positional data and force data in a minimally intrusive manner. In one aspect, the device fits into the back (or dorsal side) of the finger segment, leaving the finger pad exposed to receive haptic feedback from surface or object being interacted with. This design does not obstruct the finger pads (i.e. volar aspects), nor does it interfere with the normal tactile sensation of the human finger. The device also functions normally when used underneath a surgical glove, or between an examination glove and a surgical glove, meaning that the device does not require contact with the user's skin. This device may play a crucial role in measuring and quantifying proficiency with a wide variety of surgical instruments. This aspect of the invention allows a user to quantify and map the shape and topography of any rigid or semi-rigid object by touching or palpating it with one or more fingers. This aspect of the invention can also be used to quantify grip force at the fingers, as well as the central force point location.

In one aspect, the present invention is compatible with a minimally invasive approach because it can be used blindly (i.e. only by feel). This allows a surgeon to insert his/her finger into the patient's anatomy through a minimally invasive portal in order to digitize the bony surfaces by touch alone.

In another aspect, the present invention may be used to measure dexterity, including finger segment movements and applied forces, for specific tasks. This aspect has applications in quantifying tasks performed by experienced surgeons in order to train surgical trainees. The invention also has applications in industry and manufacturing as it may be used for quantifying manual production tasks.

In another aspect, the present invention may be used to reverse engineer parts or assemblies for mathematical or graphical representation in computer-aided design (CAD) applications, and for subsequent fabrication of similar parts or assemblies. The invention can resolve a precise point of surface contact using finger tissue deformation as well as transforming that contact point to a reference measurement frame. This capability is useful for measuring the topography of an object's surface.

Figure 1:
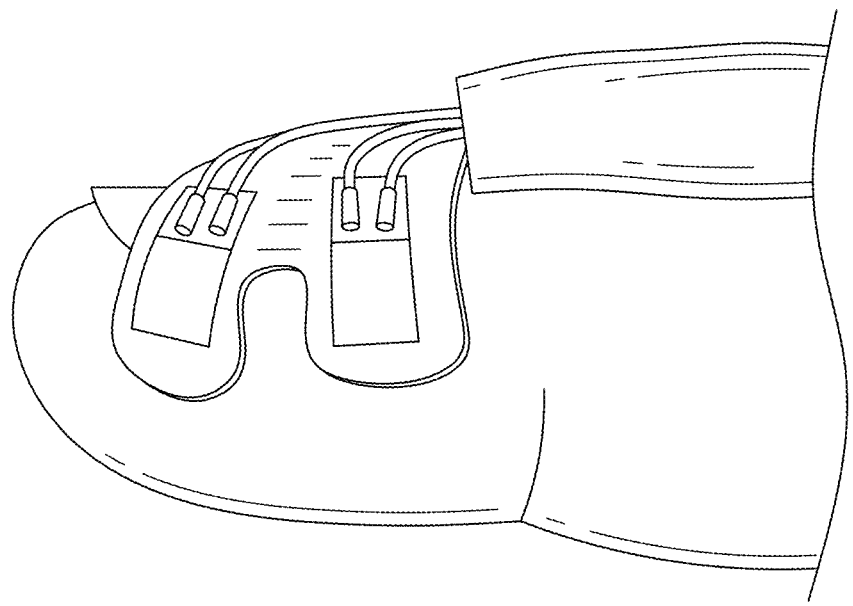
FIG. 1 is a side view of a device according to one aspect of the invention.
Figure 1A:
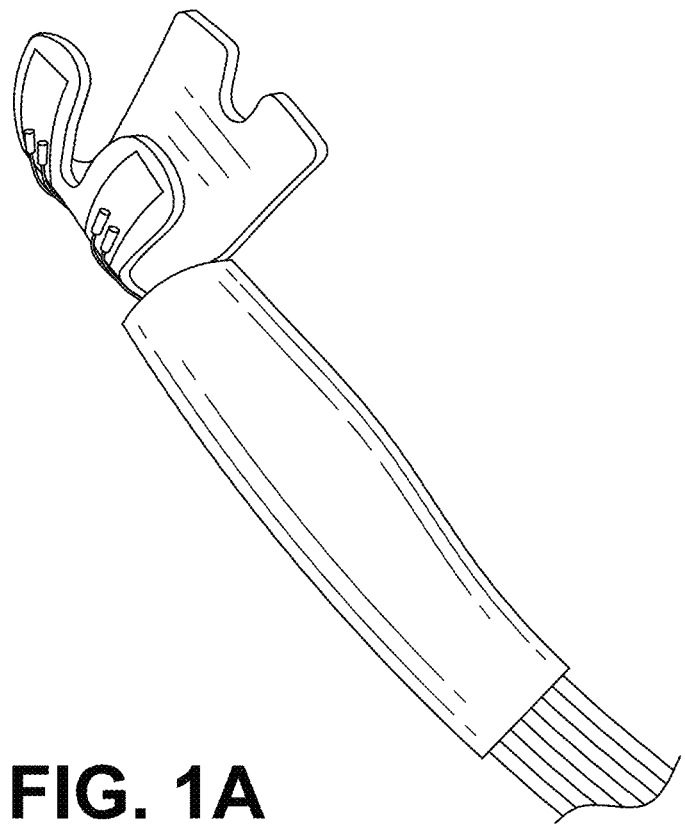
FIG. 1A is a view of the device in FIG. 1 in isolation.
Figure 1B:
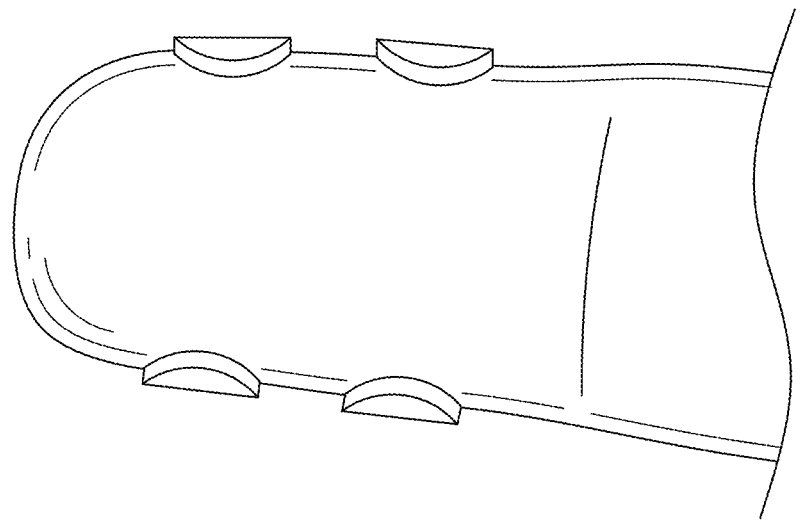
FIG. 1B is a bottom view of the finger in FIG. 1 with the device deployed.

Referring to FIG. 1, a side view of the one aspect of the invention is provided. As can be seen from the figure, the device is worn on the back of a finger segment. In FIG. 1, the device is worn on the most distal finger segment over the nail. The device may also be worn at other finger segments between the joints or knuckles, and multiple instances of the device may be worn on separate fingers or on different segments of the same finger. The design of the invention allows the user to feel the object using his/her finger pads, and the device does not interfere with the high fidelity tactile sensitivity possessed by humans. A user can comfortably wear the device and feel or grasp objects freely. A view of the device without being worn on a finger segment is provided in FIG. 1A. A view of the finger segment with the device deployed is illustrated in FIG. 1B. As can be seen, the device does not block the finger pad from direct contact with the surface of an object. The sensors (strain gauges in this implementation) are positioned at the sides of the finger segment with two sensors on the left side of the finger segment and another two sensors on the right side of the finger segment. Depending on the implementation, some strain gauges may only require that tabs attached to the gauges be at the sides of the finger segment.

Figure 2:
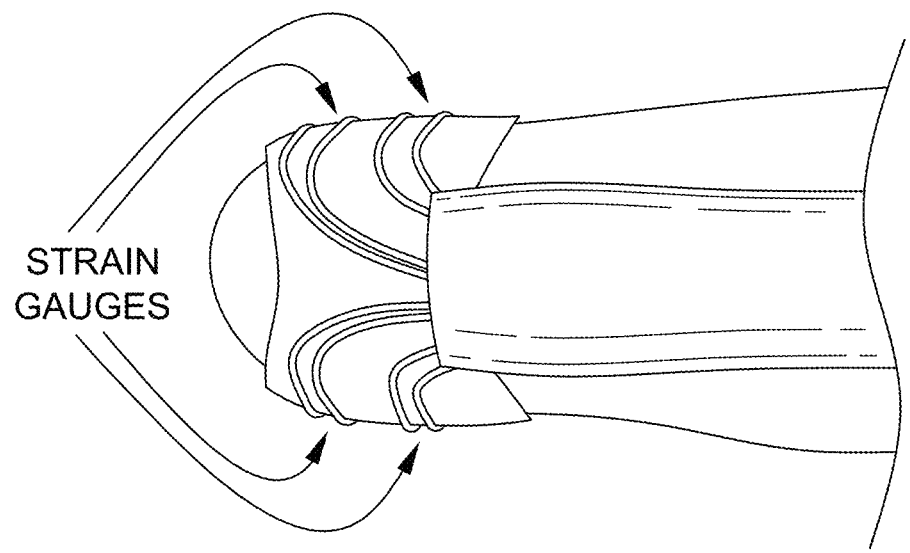
FIG. 2 is a top view of the device in FIG. 1 illustrating the sensors used in the device.
Figure 3:
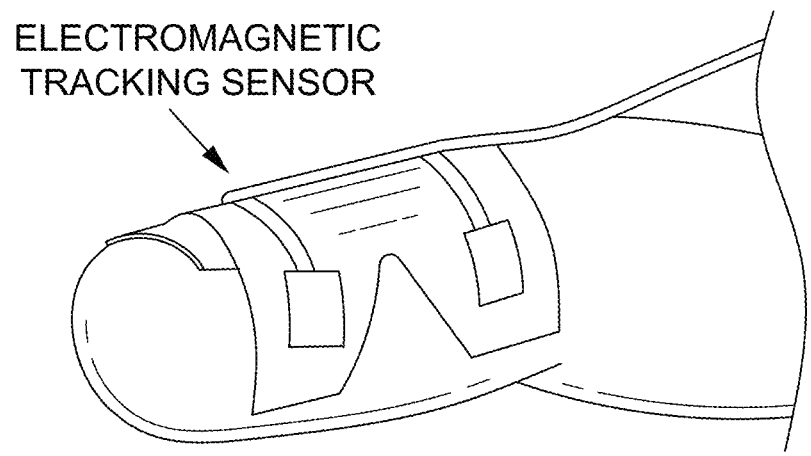
FIG. 3 is an isometric view of the device deployed on the distal segment of a finger and illustrating the location of the positioning sensor.

Referring to FIG. 2, in one embodiment, the present invention has four strain gauges positioned at the periphery or the sides of a finger segment. In FIG. 2, the device is used on the most distal finger segment with the four strain gauges being positioned at four quadrants of the finger segment. Also present in the device is a positioning sensor, not shown in FIG. 2. Referring to FIG. 3, an illustration showing two of the strain gauges and the positioning sensor is presented. It should be noted that while the Figures illustrate the use of four sensors in the form of strain gauges, other numbers of sensors may be used. As well, other types of sensors other then strain gauges may be used. As one example, liquid embedded elastomer electronics as soft curvature sensors may be used in place of the strain gauges. As another example, piezoelectric or capacitive sensors may also be used.

The device works on the principle that when a finger or finger segment touches an object, the finger pad tissue (also known as the digital pulp) gets compressed. This causes a widening of the overall tissue surrounding the finger segment. This happens because the total volume of tissue remains nearly constant. The stress that this tissue deformation places on the device is measured using extremely sensitive strain gauges or other similar sensors, such as those which utilize the piezoelectric effect or the capacitive effect. Four strain gauges measure tissue deformation at four quadrants (see FIG. 2). The sensors produce a signal that is proportional to the amount of deformation of the finger pad tissue. Similarly, each of the sensors produce a signal proportional to the sensor's distance from the centroid of the deformation. Because of this, the relative ratio of deformation measured among the various gauges can be used to indicate the location of the centroid point of surface contact in the 2-dimensional plane of FIG. 2. The overall magnitude of deformation detected by the sensors is used to indicate the third dimension (i.e. into the finger tissue) of the centroid location of the point of contact. Thus, complete 3-dimensional localization of the centroid point of surface contact is measured relative to the group of sensors. As an example of the concept of how the centroid point of surface contact is localized, consider a square trampoline whose membrane is supported by four corner posts. Each corner post is subjected to the force which supports a person on the trampoline. When all four posts experience equal force, then this is an indication that the person is located in the center. If the four post forces increase but remain equal, then this indicates that the person is descending deeper into the trampoline. If the two posts on the left side experience 20% more force equally, compared to the opposite posts on the right side, then this indicates that the person is closer to the left side. If the person moves closer to the top post while maintaining the same proximity to the left side, then this will be indicated by the top-left supporting the majority of the force, while the forces detected on the other posts change accordingly.

Using the concept explained above, the device can be used to measure the centroid surface contact point in relation to the finger segment. In order to relate the contact point to an absolute global location, a tracking sensor is integrated into the device (see FIG. 3). In one implementation, an electromagnetic tracking sensor is used. For this example tracking system, an electromagnetic field is used to determine where the sensor is located and how it is oriented. The electromagnetic tracking system transmits three electromagnetic fields which correspond to three orthogonal axes (x,y,z) of the transmitter's reference frame. The tracking sensor on the device contains three orthogonal antennae which correspond to three orthogonal axes (x,y,z) of the tracking sensor's reference frame. The transmitted electromagnetic fields induce electric currents in the antennae. The system interprets relative ratios of current magnitudes as misalignments of the sensor's frame with the transmitter's frame as orientation angles. The system also interprets overall magnitudes of the induced currents as distances of the sensor's frame relative to the axes of the transmitter's frame. Of course, other types of tracking sensors and tracking systems may be used.

Once the device has been calibrated, the integrated system can report the location of the contact point relative to any predetermined reference frame.

Figure 4:
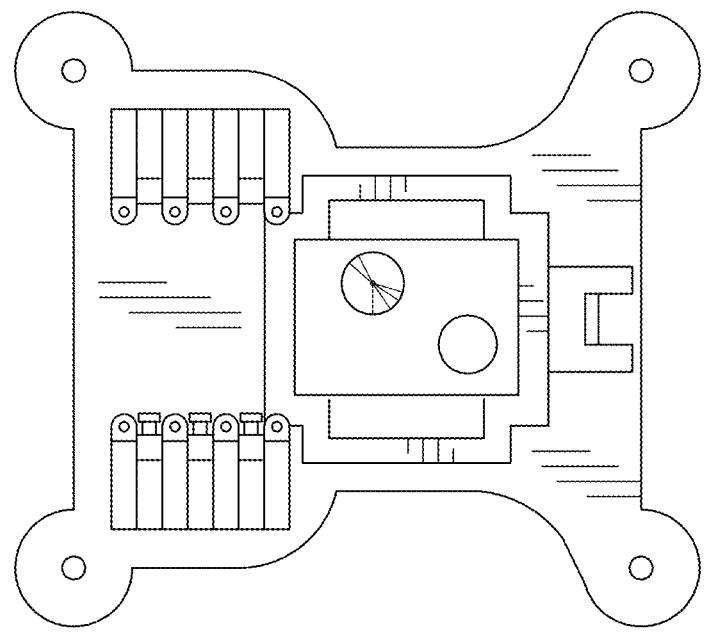
FIG. 4 is an illustration of the calibration jig used to calibrate the device in FIG. 1.
Figure 4:
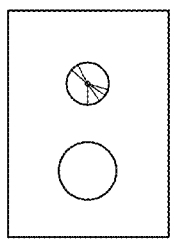
Figure 4:
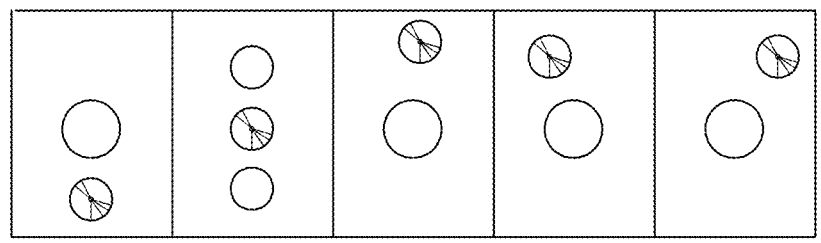
Figure 5:
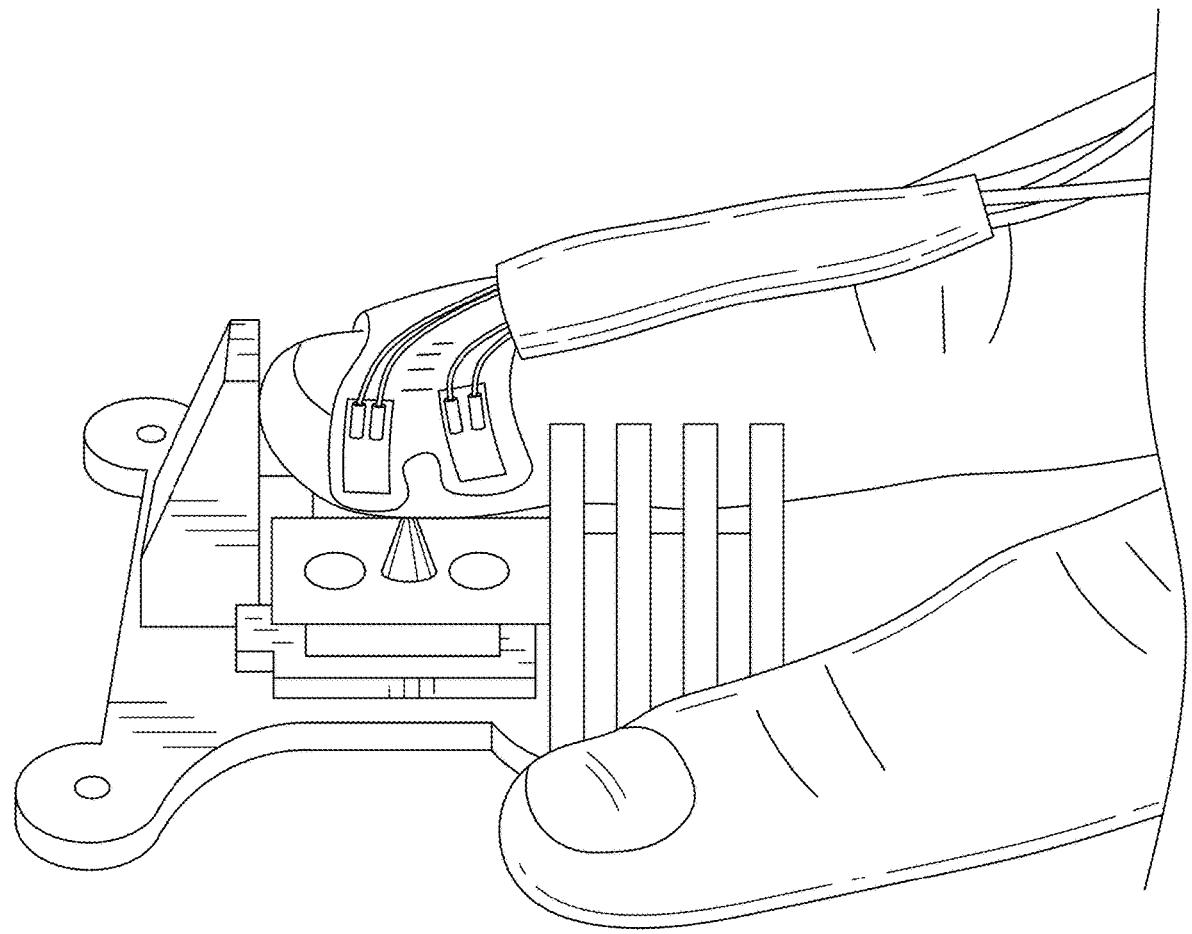
FIG. 5 shows the device deployed on a finger segment and positioned on the calibration jig in FIG. 4.

As noted above, the device sits on the top of the finger segment and uses four strain gauges to determine deformation on the finger pad. A local coordinate frame was created relative to the finger segment to calibrate the system, as well as to locate position. The y-axis is directed along the length of the finger distally and the x-axis is directed across the finger's width. The local coordinate frame was created using points digitized on the fingertip surface with the aid of a calibration jig. The calibration jig is illustrated in FIG. 4. FIG. 5 illustrates the device worn on a finger segment and placed in the calibration jig.

Figure 6:
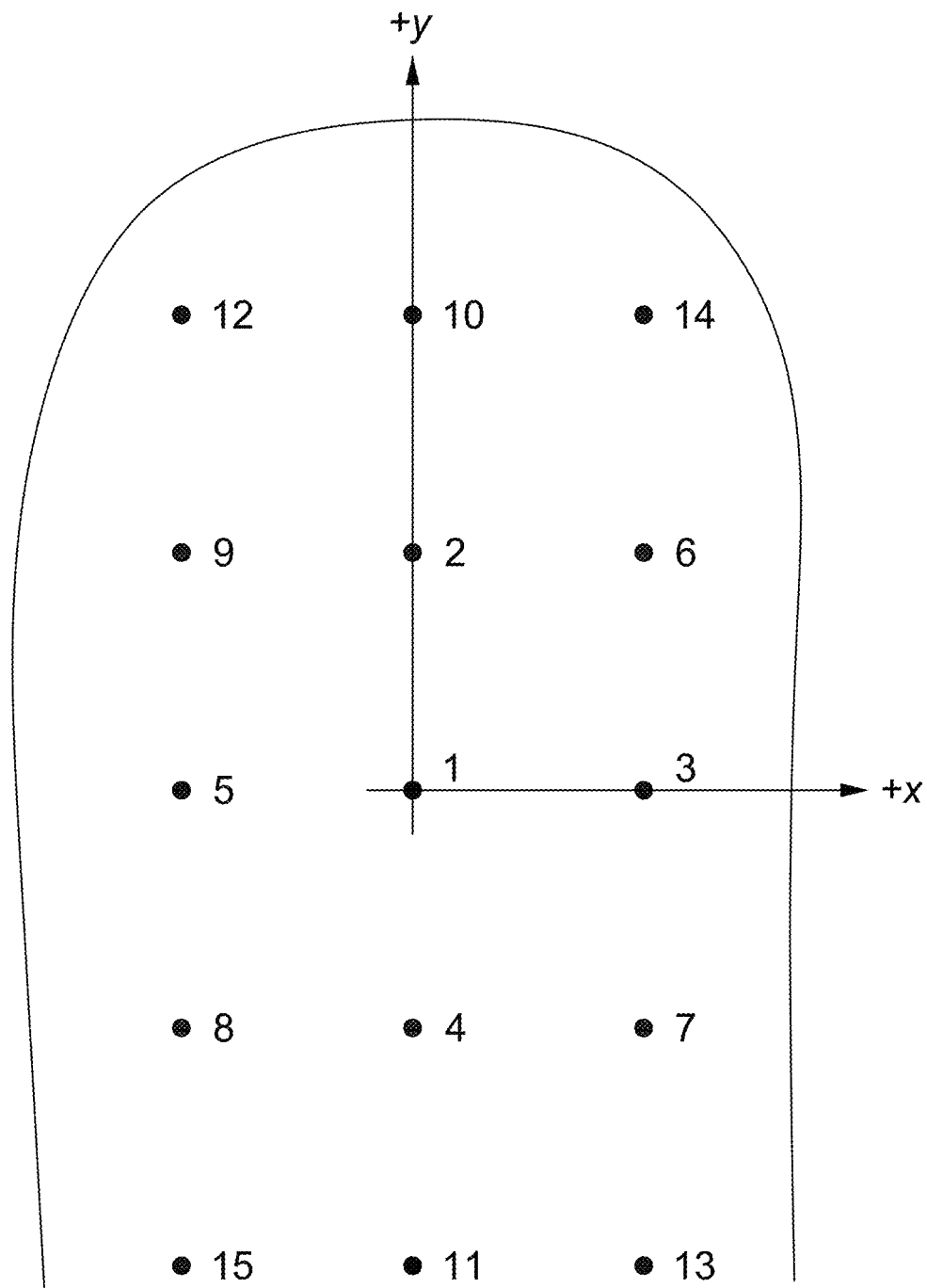
FIG. 6 illustrates a map of the calibration points on the distal finger segment.

FIG. 6 illustrates a map which indicates all the calibration points in the finger's local coordinate system. Transforming this coordinate frame to the electromagnetic tracker allowed for real time measurements on the surface of the finger.

The digitizer uses finger strain to calculate the location of the net contact point. The digitizer includes the positional sensor (in this embodiment a small electromagnetic tracker) that allows the contact point's location to be measured relative to a global coordinate frame. This means that the finger's contact point can be reported relative to a predetermined reference frame (e.g. a patient's body frame in the case of physiotherapy) or relative to an assembly (e.g. in the case of a manual manufacturing process).

The calibration jig was also mounted on a six degree-of-freedom load cell transducer in order to calibrate for contact force as well. This means that the finger digitizer reports contact force as well as the location of the contact point.

Experiments have shown that position measurements had errors ranging from 0.48 to 4.39 mm with an average error of 2.02 mm.

Similar experiments have shown that force measurements had maximum errors of 0.31 to 1.24 N with an average error of 0.17 N. Both the maximum and average force errors increased with increasing applied force.

When in use, the device allows surface contact points to be streamed in real-time to software that builds the surface on a visual feedback monitor or an image of the surface can be projected to a three-dimensional screen (i.e. projection screen or 3D goggles). The strain-gauge monitoring software can be set with a calibrated force threshold in order to identify finger contact with a surface. Thus, the streaming surface data is only recorded when contact is maintained. In this way, the digitized surface is rendered visually in real-time as the user palpates (i.e. touches) the object.

It should be noted that the black backing shown in FIGS. 1 and 2 contains the terminal connections for a prototype cable. Other implementations of the device may use very thin and flexible cables and may not require the backing. This is illustrated in FIG. 3.

As a grip force measurement device, the device can be used to quantify the force of any finger segment as a function of location on the finger.

The force measurement and contact point location capabilities of the device can be used simultaneously. In this way, the amount of force and the location of contact force on any finger segment can be measured while simultaneously digitizing the 3-dimensional locations as a function of the contact force. This can provide a 4-dimensional surface contact map, with the 4th dimension representing the contact force. The 4th dimension is commonly indicated by color changes.

In one implementation, multiple instances of the device are simultaneously used on different segments of different fingers of the user. As an example, the distal segments of the thumb, index, and middle fingers of the user are each provided with one instance of the device. As well, the intermediate segments of the index and middle fingers are also provided with instances of the device. This allows the user to have the movements, location, and force felt by his or her most used fingers to be tracked. Such a configuration would be useful as a training tool. In one example, a surgical expert could be equipped with multiple instances of the device while performing a procedure to have his or her finger movements tracked. Students and trainees can then mimic the movements as well as the "touch" of the surgical expert so as to learn the proper method for executing the procedure. It should be noted that this configuration would also be able to track finger flexion and finger extension (which themselves will deform a single finger segment to some extent). Flexions and extensions are detected through the location sensing and relative comparison of each finger segment unit—changes due to the flexion are measured by the strain gauges. This configuration may also be used for training medical practitioners on certain physical procedures such as patient examinations or massages. The expert's "touch", e.g. how hard to squeeze where on what kind of patient can be quantified. A trainee can also benefit by having his or her "touch" quantified so that his or her performance can be assessed against the expert's performance. However, applications are possible in any area that has expert practitioners using very fine motor skills that need to be transferred to trainees. For such an implementation, each device worn on a finger segment would, of course, be independently tracked and its readings gathered independent of the other devices on the other finger segments.

As noted above, the device is also suitable for applications in which a user wishes to quantify the shape and topography of any rigid or semi-rigid object surface. Once digitized, the surface of any object can be virtually generated and manipulated using engineering Computer Assisted Design (CAD) or any other surface editing software. This makes the device appropriate for reverse-engineering tasks.

The device is also suitable for applications that require finger contact force measurement. In addition to measuring force at any finger segment, the force can also be mapped as a function of location on the finger segment. This mode of operation can be useful in the following areas:

1) assembly quality control and training
2) surgical technique simulation training
3) physiotherapy training and confirmation
4) video games In addition to the above advantages, the device can be used without a line-of-sight to the surface being digitized.

This allows the user to digitize an object by touch alone. The device fits compactly onto a finger and can easily be worn under surgical gloves.

It allows a user to feel the object without obstructing the finger pad from making contact with the object.

The device aspect of the invention has already been tested while wearing one or two surgical gloves over it. It will also function overtop a surgical glove and under an additional surgical glove, thereby interposing the device between the two gloves. This flexibility is important in surgical applications. This allows users to preclude skin contact with the device at their own discretion.

When used in force measurement applications, the device does not go between the user's finger and the object being grasped. Thus, the user still feels the object unobstructed. This is an advantage over surface force technologies such as Tekscan® (Tekscan Inc., South Boston, Mass.), Pliance® (Novel, gmbh, Munich) and FingerTPS II® (Force Profile Systems Inc., Los Angeles, Calif.).

The location tracking capabilities allow the device to record the motion of any finger segment. The point contact capability allows it to measure the centroid contact point of any finger segment relative to the finger and relative to any arbitrary reference.

The force mapping capability allows it to map contact force relative to the finger and relative to any arbitrary reference.

It should be noted that the invention may also be used to detect and measure user's pulse. The user's pulse is measured in the same way that the overall contact force is measured. The systolic pressure rise (i.e. heart beat) causes the finger tissue to swell slightly. This internal pressure swell is detected as an overall deformation of the finger tissue. The periodic nature of the pulse renders the pulse signal quite distinct from the tissue distortion caused by contact forces. The pulse is therefore readily detected and measured while the device is in normal use. Reading the pulse does not interfere with any of the other functions of the device and the pulse measurement can occur simultaneously with the device's other functions.

In another aspect, the present invention relates to a method for determining a feature on a surface being mapped using the device described above. The method begins with detecting a deformation of a finger segment pad. This deformation causes one or more of the sensors deployed around the finger segment to trigger. The amount of deformation detected by a sensor depends on the location of the feature—the closer the sensor is to the feature, the greater the amount of deformation detected. By correlating the various deformation readings (e.g. by using ratios between readings from different sensors) the centroid of the feature can be determined. The height/depth of the feature can also be determined by finding the largest deformation reading from the various sensors within a given time frame from the triggering of the sensors. The larger the deformation, the larger the largest reading should be. The location of the feature can then be determined on a global coordinate grid by reading the location from the positioning sensor on the device. Two software packages were developed for use with this system. Calibration software works in conjunction with the calibration jig (FIGS. 4 and 5) to calibrate the force and point of contact relative to the finger segment. The calibration jig utilizes modular contact points (FIG. 4) which correspond to predetermined locations relative to the finger segment (FIG. 6). The calibration software guides the user to follow a sequence of predetermined contact points (FIG. 6) while the software measures both the actual applied force and its contact point. The calibration data is saved for transfer to the real-time measurement software. Once the system is calibrated, real-time measurement software measures contact force and point of contact. This software interfaces with the positional tracking system as well as the strain sensors of the finger segment device. The real-time measurement software uses the force calibration data to calculate the point of contact relative to the finger segment, and it uses the location calibration data to transform that point of contact to a desired reference frame on any object that is measurable by the tracking system. Both the calibration software and the real-time measurement software can be operated using only one method of measurement, either force or location. If only force is measured, then the force and local contact point relative to the finger segment can be calculated and output by the software. If only location data is utilized, then the location of any calibrated point on the finger segment can be tracked in real-time. It should, however, be noted that this calibrated point does not change with finger deformation and it is at a constant local location relative to the finger segment device.

The embodiments of the invention may be executed by a computer processor or similar device programmed in the manner of method steps, or may be executed by an electronic system which is provided with means for executing these steps. Similarly, an electronic memory means such as computer diskettes, CD-ROMs, Random Access Memory (RAM), Read Only Memory (ROM) or similar computer software storage media known in the art, may be programmed to execute such method steps. As well, electronic signals representing these method steps may also be transmitted via a communication network.

Embodiments of the invention may be implemented in any conventional computer programming language. For example, preferred embodiments may be implemented in a procedural programming language (e.g. "C") or an object-oriented language (e.g. "C++", "java", "PHP", "PYTHON", "LabVIEW" or "C#"). Alternative embodiments of the invention may be implemented as pre-programmed hardware elements, other related components, or as a combination of hardware and software components.

Embodiments can be implemented as a computer program product for use with a computer system. Such implementations may include a series of computer instructions fixed either on a tangible medium, such as a computer readable medium (e.g., a diskette, CD-ROM, ROM, or fixed disk) or transmittable to a computer system, via a modem or other interface device, such as a communications adapter connected to a network over a medium. The medium may be either a tangible medium (e.g., optical or electrical communications lines) or a medium implemented with wireless techniques (e.g., microwave, infrared or other transmission techniques). The series of computer instructions embodies all or part of the functionality previously described herein. Those skilled in the art should appreciate that such computer instructions can be written in a number of programming languages for use with many computer architectures or operating systems. Furthermore, such instructions may be stored in any memory device, such as semiconductor, magnetic, optical or other memory devices, and may be transmitted using any communications technology, such as optical, infrared, microwave, or other transmission technologies. It is expected that such a computer program product may be distributed as a removable medium with accompanying printed or electronic documentation (e.g., shrink-wrapped software), preloaded with a computer system (e.g., on system ROM or fixed disk), or distributed from a server over a network (e.g., the Internet or World Wide Web). Of course, some embodiments of the invention may be implemented as a combination of both software (e.g., a computer program product) and hardware. Still other embodiments of the invention may be implemented as entirely hardware, or entirely software (e.g., a computer program product).

A person understanding this invention may now conceive of alternative structures and embodiments or variations of the above all of which are intended to fall within the scope of the invention as defined in the claims that follow.

We claim:

1. A system for measuring force exerted on multiple fingers of a user, the system comprising:
 a plurality of devices for detecting and measuring force on one of said user's finger segments, each device comprising:
  a plurality of sensors for detecting a deformation of a pad on a finger segment, each one of said plurality of sensors producing a signal proportional to an amount of said deformation detected and proportional to a distance between said deformation and said one of said plurality of sensors; and
  a positional sensor for determining a location of said one of said plurality of devices relative to a predetermined reference frame,
 wherein each of said plurality of devices is deployed on a separate finger segment of said user,
 wherein said plurality of sensors comprises four sensors, and
 wherein two sensors are positioned at a left side of said finger segment and two sensors are positioned at a right side of said finger segment.

2. A system according to claim 1, wherein said plurality of sensors comprises strain gauges.

3. A system according to claim 1, wherein said positional sensor is located on top of said finger segment.

* * * * *